US007750011B2

(12) United States Patent
Peters et al.

(10) Patent No.: US 7,750,011 B2
(45) Date of Patent: Jul. 6, 2010

(54) DIAZABICYCLIC ARYL DERIVATIVES AND THEIR MEDICAL USE

(75) Inventors: Dan Peters, Malmö (DK); Daniel B. Timmermann, Herlev (DK); Gunnar M. Olsen, Smørum (DK); Elsebet Østergaard Nielsen, København (DK); Tino Dyhring, Solrød (DK)

(73) Assignee: Neurosearch A/S, Ballerup (DK)

( * ) Notice: Subject to any disclaimer, the term of this patent is extended or adjusted under 35 U.S.C. 154(b) by 0 days.

(21) Appl. No.: 11/884,345

(22) PCT Filed: Feb. 13, 2006

(86) PCT No.: PCT/EP2006/050873

§ 371 (c)(1),
(2), (4) Date: Oct. 1, 2007

(87) PCT Pub. No.: WO2006/087305

PCT Pub. Date: Aug. 24, 2006

(65) Prior Publication Data

US 2008/0161314 A1 Jul. 3, 2008

Related U.S. Application Data

(60) Provisional application No. 60/653,512, filed on Feb. 17, 2005.

(30) Foreign Application Priority Data

Feb. 15, 2005  (DK) ................................ 2005 00229

(51) Int. Cl.
C07D 403/04 (2006.01)
C07D 401/04 (2006.01)
C07D 409/04 (2006.01)
C07D 405/14 (2006.01)
A61K 31/501 (2006.01)
A61K 31/497 (2006.01)
A61P 21/00 (2006.01)
A61P 5/00 (2006.01)
A61P 25/00 (2006.01)
A61P 29/00 (2006.01)

(52) U.S. Cl. .......................... 514/252.02; 514/255.05; 544/238; 544/405

(58) Field of Classification Search ............ 514/252.03, 514/252.02, 255.05; 544/238, 405
See application file for complete search history.

(56) References Cited

U.S. PATENT DOCUMENTS 5,478,939 A  12/1995  Trybulski et al.
6,635,645 B1  10/2003  Lochead et al.

FOREIGN PATENT DOCUMENTS

| EP | 1 359 152 A | 11/2003 |
|---|---|---|
| WO | WO-99/42465 A2 | 8/1999 |
| WO | WO-00/34284 A1 | 6/2000 |
| WO | WO-00/44755 A1 | 8/2000 |
| WO | WO-03/94831 A2 | 11/2003 |
| WO | WO-2004/029053 A1 | 4/2004 |
| WO | WO-2004/043960 A1 | 5/2004 |
| WO | WO-2005/011654 A | 2/2005 |
| WO | WO-2005/011657 A | 2/2005 |
| WO | WO-2005/074940 A1 | 8/2005 |

OTHER PUBLICATIONS

Palmen, et al., Brain 2004 127(12):2572-2583.*
See, et al., Neuroscience, vol. 117, Issue 2, Mar. 21, 2003, pp. 477-483.*
Harvey, et al., J Neurophysiol 96: 1171-1186, 2006.*

* cited by examiner

*Primary Examiner*—James O Wilson
*Assistant Examiner*—Cecilia M Jaisle
(74) *Attorney, Agent, or Firm*—Birch, Stewart, Kolasch & Birch, LLP

(57) ABSTRACT

This invention relates to novel diazabicyclic aryl derivatives which are found to be cholinergic ligands at the nicotinic acetylcholine receptors and modulators of the monoamine receptors and transporters. Due to their pharmacological profile the compounds of the invention may be useful for the treatment of diseases or disorders as diverse as those related to the cholinergic system of the central nervous system (CNS), the peripheral nervous system (PNS), diseases or disorders related to smooth muscle contraction, endocrine diseases or disorders, diseases or disorders related to neurodegeneration, diseases or disorders related to inflammation, pain, and withdrawal symptoms caused by the termination of abuse of chemical substances.

16 Claims, No Drawings

DIAZABICYCLIC ARYL DERIVATIVES AND THEIR MEDICAL USE

This application is the National Phase of PCT application PCT/EP2006/050873, filed Feb. 13, 2006 and claims priority under 35 U.S.C. 119(e) to U.S. Provisional Application No. 60/653,512 filed on Feb. 17, 2005 and under 35 U.S.C. 119(a) to Patent Application No. PA 2005-00229 filed in Denmark on Feb. 16, 2005. Both of these prior applications are hereby expressly incorporated by reference into the present application.

TECHNICAL FIELD

This invention relates to novel diazabicyclic aryl derivatives, which are found to be cholinergic ligands at the nicotinic acetylcholine receptors and modulators of the monoamine receptors and transporters. Due to their pharmacological profile the compounds of the invention may be useful for the treatment of diseases or disorders as diverse as those related to the cholinergic system of the central nervous system (CNS), the peripheral nervous system (PNS), diseases or disorders related to smooth muscle contraction, endocrine diseases or disorders, diseases or disorders related to neuro-degeneration, diseases or disorders related to inflammation, pain, and withdrawal symptoms caused by the termination of abuse of chemical substances.

BACKGROUND ART

The endogenous cholinergic neurotransmitter, acetylcholine, exert its biological effect via two types of cholinergic receptors, the muscarinic Acetyl Choline Receptors (mAChR) and the nicotinic Acetyl Choline Receptors (nAChR).

As it is well established that muscarinic acetylcholine receptors dominate quantitatively over nicotinic acetylcholine receptors in the brain area important to memory and cognition, and much research aimed at the development of agents for the treatment of memory related disorders have focused on the synthesis of muscarinic acetylcholine receptor modulators.

Recently, however, an interest in the development of nAChR modulators has emerged. Several diseases are associated with degeneration of the cholinergic system i.e. senile dementia of the Alzheimer type, vascular dementia and cognitive impairment due to the organic brain damage disease related directly to alcoholism. Indeed several CNS disorders can be attributed to a cholinergic deficiency, a dopaminergic deficiency, an adrenergic deficiency or a serotonergic deficiency.

U.S. Pat. No. 5,478,939, WO 00/34284 and WO 00/44755 describe 2,5-diazabicyclo[2.2.1]heptane derivatives having affinity for nicotinic receptors. However, the diazabicyclic aryl derivatives of the invention have not been reported.

SUMMARY OF THE INVENTION

The present invention is devoted to the provision novel modulators of the nicotinic and/or of the monoamine receptors, which modulators are useful for the treatment of diseases or disorders related to the cholinergic receptors, and in particular the nicotinic acetylcholine receptor (nAChR), the serotonin receptor (5-HTR), the dopamine receptor (DAR) and the norepinephrine receptor (NER), and of the biogenic amine transporters for serotonin (5-HT), dopamine (DA) and norepinephrine (NE).

Due to their pharmacological profile the compounds of the invention may be useful for the treatment of diseases or disorders as diverse as those related to the cholinergic system of the central nervous system (CNS), the peripheral nervous system (PNS), diseases or disorders related to smooth muscle contraction, endocrine diseases or disorders, diseases or disorders related to neuro-degeneration, diseases or disorders related to inflammation, pain, and withdrawal symptoms caused by the termination of abuse of chemical substances.

The compounds of the invention may also be useful as diagnostic tools or monitoring agents in various diagnostic methods, and in particular for in vivo receptor imaging (neuroimaging), and they may be used in labelled or unlabelled form.

In its first aspect the invention provides novel (R,R) or (S,S) 2,5-diaza-bicyclo[2.2.1]heptane aryl derivatives represented by Formula I

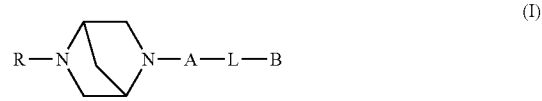

(I)

or an enantiomer or a mixture of its enantiomers, or a pharmaceutically acceptable salt thereof, or an aza-onium salt thereof, wherein R represents hydrogen, alkyl, cycloalkyl or cycloalkyl-alkyl;

A represents an aromatic monocyclic or bicyclic carbocyclic or heterocyclic group, which carbocyclic or heterocyclic groups are optionally substituted one or more times with substituents selected from the group consisting of alkyl, cycloalkyl, cycloalkyl-alkyl, hydroxy, alkoxy, cyanoalkyl, halo, trihaloalkyl, trihaloalkoxy, cyano, amino and nitro;

B represents a phenyl or naphthyl group, a 5-6 membered aromatic monocyclic heterocyclic group, or an aromatic bicyclic heterocyclic group; which aromatic groups may optionally be substituted one or more times with substituents selected from the group consisting of alkyl, cycloalkyl, hydroxy, alkoxy, cyanoalkyl, halo, trihaloalkyl, trihaloalkoxy, cyano, amino, nitro, and —NH(CO)R'; wherein R' represents hydrogen, alkyl or cycloalkyl; and L represents —O—, —S—, —S—CH$_2$—, —CH$_2$—S—, —SO—, —SO$_2$—, —NR"—, —CH$_2$—, —CH$_2$—CH$_2$—, —CH=CH—, —C≡C—, —NR"CO—, —NR"CONR"— or —NR"(SO$_2$)—; wherein R" represents hydrogen or alkyl.

In its second aspect the invention provides pharmaceutical compositions comprising a therapeutically effective amount of the diazabicycloheptane aryl derivative of the invention, or a pharmaceutically-acceptable addition salt thereof, together with at least one pharmaceutically-acceptable carrier or diluent.

In a further aspect the invention relates to the use of the diazabicycloheptane aryl derivative of the invention, or a pharmaceutically-acceptable addition salt thereof, for the manufacture of a pharmaceutical composition/medicament for the treatment, prevention or alleviation of a disease or a disorder or a condition of a mammal, including a human, which disease, disorder or condition is responsive to modulation of cholinergic receptors and/or monoamine receptors.

In a final aspect the invention provides methods of treatment, prevention or alleviation of diseases, disorders or conditions of a living animal body, including a human, which disorder, disease or condition is responsive to modulation of cholinergic receptors and/or monoamine receptors, which method comprises the step of administering to such a living animal body in need thereof a therapeutically effective amount of the diazabicycloheptane aryl derivative of the invention.

Other objects of the invention will be apparent to the person skilled in the art from the following detailed description and examples.

DETAILED DISCLOSURE OF THE INVENTION

Diazabicyclic Aryl Derivative

In a first aspect novel (R,R) or (S,S) 2,5-diaza-bicyclo [2.2.1]heptane aryl derivatives are provided. The diazabicycloheptane aryl derivatives of the invention may be represented by the general Formula I

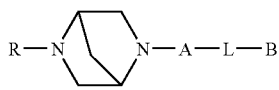

(I)

or an enantiomer or a mixture of its enantiomers, or a pharmaceutically acceptable salt thereof, or an aza-onium salt thereof, wherein R represents hydrogen, alkyl, cycloalkyl or cycloalkyl-alkyl;

A represents an aromatic monocyclic or bicyclic carbocyclic or heterocyclic group, which carbocyclic or heterocyclic groups are optionally substituted one or more times with substituents selected from the group consisting of alkyl, cycloalkyl, cycloalkyl-alkyl, hydroxy, alkoxy, cyanoalkyl, halo, trihaloalkyl, trihaloalkoxy, cyano, amino and nitro;

B represents a phenyl or naphthyl group, a 5-6 membered aromatic monocyclic heterocyclic group, or an aromatic bicyclic heterocyclic group; which aromatic groups may optionally be substituted one or more times with substituents selected from the group consisting of alkyl, cycloalkyl, hydroxy, alkoxy, cyanoalkyl, halo, trihaloalkyl, trihaloalkoxy, cyano, amino, nitro, and —NH(CO)R'; wherein R' represents hydrogen, alkyl or cycloalkyl; and L represents —O—, —S—, —S—CH$_2$—, —CH$_2$—S—, —SO—, —SO$_2$—, —NR"—, —CH$_2$—, —CH$_2$—CH$_2$—, —CH=CH—, —C≡C—, —NR"CO—, —NR"CONR"— or —NR" (SO$_2$)—; wherein R" represents hydrogen or alkyl.

In a preferred embodiment diazabicycloheptane aryl derivative of the invention is represented by Formula I, wherein R represents hydrogen, alkyl, cycloalkyl or cycloalkyl-alkyl.

In a more preferred embodiment R represents hydrogen or alkyl.

In an even more preferred embodiment R represents hydrogen, methyl or ethyl.

In another preferred embodiment diazabicycloheptane aryl derivative of the invention is represented by Formula I, wherein A represents an aromatic monocyclic or bicyclic carbocyclic or heterocyclic group, which carbocyclic or heterocyclic groups are optionally substituted one or more times with substituents selected from the group consisting of alkyl, cycloalkyl, cycloalkyl-alkyl, hydroxy, alkoxy, cyanoalkyl, halo, trihaloalkyl, trihaloalkoxy, cyano, amino and nitro.

In a more preferred embodiment A represents a phenyl group.

In another more preferred embodiment A represents a 5-membered aromatic monocyclic heterocyclic group selected from furanyl, thienyl, pyrrolyl, oxazolyl, thiazolyl, imidazolyl, pyrazolyl, isoxazolyl, isothiazolyl, oxadiazolyl, triazolyl and thiadiazolyl.

In an even more preferred embodiment A represents a thiadiazolyl group, in particular 1,3,4-thiadiazol-2,5-diyl.

In a third more preferred embodiment A represents a 6-membered aromatic monocyclic heterocyclic group selected from pyridyl, pyridazinyl, pyrimidinyl, pyrazinyl and triazinyl.

In an even more preferred embodiment A represents a pyridin-2,5-diyl group, a pyridin-3,6-diyl group, a pyridazin-3,6-diyl group, a pyrimidin-2,4-diyl group, a pyrimidin-4,5-diyl group, a pyrazin-2,5-diyl group, a pyrazin-2,6-diyl group or a triazin-2,4-diyl group.

In a fourth more preferred embodiment A represents a phenyl, a thiadiazolyl, a pyridyl or pyridazinyl group.

In a fifth more preferred embodiment A represents a thiadiazolyl group, in particular 1,3,4-thiadiazol-2,5-diyl; a pyridinyl group, in particular pyrimidine-2,5-diyl; a pyridazinyl group, in particular pyridazin-3,6-diyl or pyridazin-3,5-diyl; a pyrimidinyl group, in particular pyrimidin-2,5-diyl; or a pyrazinyl group, in particular pyrazin-2,5-diyl.

In a sixth more preferred embodiment A represents a phenyl, a thiadiazolyl, a pyridinyl or pyridazinyl group.

In a seventh more preferred embodiment A represents a pyridazinyl group, in particular pyridazin-3,6-diyl or pyridazin-3,5-diyl.

In a third preferred embodiment the diazabicycloheptane aryl derivative of the invention is represented by Formula I, wherein B represents a phenyl or naphthyl group, a 5-6 membered aromatic monocyclic heterocyclic group, or an aromatic bicyclic heterocyclic group; which aromatic groups may optionally be substituted one or more times with substituents selected from the group consisting of alkyl, cycloalkyl, hydroxy, alkoxy, cyanoalkyl, halo, trihaloalkyl, trihaloalkoxy, cyano, amino, nitro, and —NH(CO)R'; wherein R' represents hydrogen, alkyl or cycloalkyl.

In a more preferred embodiment B represents a phenyl group, a furanyl group, a thienyl group or an indolyl group; which aromatic group may optionally be substituted one or two times with substituents selected from the group consisting of alkyl, cycloalkyl, hydroxy, alkoxy, cyanoalkyl, halo, trihaloalkyl, trihaloalkoxy, cyano, amino, nitro, and —NH(CO)R'; wherein R' represents hydrogen, alkyl or cycloalkyl.

In an even more preferred embodiment B represents a phenyl group, a furanyl group, a thienyl group or an indolyl group; which aromatic group may optionally be substituted with hydroxy, alkoxy, halo, trifluoromethyl, cyano, or nitro.

In a still more preferred embodiment B represents phenyl; furanyl, in particular furan-2-yl; thienyl, in particular thieny-2-yl or thien-3-yl; or indolyl, in particular indol-5-yl; which aromatic group may optionally be substituted with hydroxy, alkoxy, halo, trifluoromethyl, cyano, or nitro.

In a yet more preferred embodiment B represents a phenyl group, a thiadiazolyl group, a pyridyl group or a pyridazinyl group; which aromatic group may optionally be substituted one or two times with substituents selected from the group consisting of alkyl, cycloalkyl, hydroxy, alkoxy, cyanoalkyl, halo, trihaloalkyl, trihaloalkoxy, cyano, amino, nitro, and —NH(CO)R'; wherein R' represents hydrogen, alkyl or cycloalkyl.

In an even more preferred embodiment B represents a phenyl group, optionally substituted one or two times with substituents selected from the group consisting of alkyl, cycloalkyl, hydroxy, alkoxy, cyanoalkyl, halo, trihaloalkyl, trihaloalkoxy, cyano, amino, nitro, and —NH(CO)R'; wherein R' represents hydrogen, alkyl or cycloalkyl.

In a yet more preferred embodiment B represents a phenyl group, optionally substituted with hydroxy, alkoxy, halo, trifluoromethyl, cyano or nitro.

In a fourth preferred embodiment diazabicycloheptane aryl derivative of the invention is represented by Formula I, wherein R represents hydrogen or alkyl; A represents thiadiazolyl, pyridinyl, pyridazinyl, pyrimidinyl or pyrazinyl; and B represents phenyl, furanyl, thienyl or indolyl; which aromatic group may optionally be substituted one or two times with substituents selected from the group consisting of alkyl, cycloalkyl, hydroxy, alkoxy, cyanoalkyl, halo, trihaloalkyl, trihaloalkoxy, cyano, amino, nitro, and —NH(CO)R'; wherein R' represents hydrogen, alkyl or cycloalkyl.

In a more preferred embodiment R represents hydrogen or alkyl; A represents thiadiazolyl, pyridinyl, pyridazinyl, pyrimidinyl or pyrazinyl; and B represents phenyl, furanyl, thienyl or indolyl; which aromatic group may optionally be substituted with hydroxy, alkoxy, halo, trifluoromethyl, cyano or nitro.

In a fifth preferred embodiment diazabicycloheptane aryl derivative of the invention is represented by Formula I, wherein R represents hydrogen or alkyl; A represents a 6-membered aromatic monocyclic heterocyclic group selected from pyridyl, pyridazinyl, pyrimidinyl, pyrazinyl and triazinyl; and B represents a phenyl group, a thiadiazolyl group, a pyridyl group or a pyridazinyl group; which aromatic group may optionally be substituted one or more times with substituents selected from the group consisting of alkyl, cycloalkyl, hydroxy, alkoxy, cyanoalkyl, halo, trihaloalkyl, trihaloalkoxy, cyano, amino, nitro and —NH(CO)R'; wherein R' represents hydrogen, alkyl or cycloalkyl.

In a sixth preferred embodiment diazabicycloheptane aryl derivative of the invention is represented by Formula I, wherein L represents —O—, —S—, —S—CH$_2$—, —CH$_2$—S—, —SO—, —SO$_2$—, —NR"—, —CH$_2$—, —CH$_2$—CH$_2$—, —CH═CH—, —C≡C—, —NR"CO—, —NR"CONR"— or —NR"(SO$_2$)—; wherein R" represents hydrogen or alkyl.

In a more preferred embodiment L represents —O—, —S—, —S—CH$_2$—, —SO—, —C≡C—, —NHCO—, —NHCONH— or —NH(SO$_2$)—.

In an even more preferred embodiment L represents —C≡C—.

In a sixth preferred embodiment diazabicycloheptane aryl derivative of the invention is represented by Formula I, wherein R represents hydrogen or alkyl; A represents thiadiazolyl, pyridinyl, pyridazinyl, pyrimidinyl or pyrazinyl; and B represents phenyl, furanyl, thienyl or indolyl; which aromatic group may optionally be substituted one or two times with substituents selected from the group consisting of alkyl, cycloalkyl, hydroxy, alkoxy, cyanoalkyl, halo, trihaloalkyl, trihaloalkoxy, cyano, amino, nitro, and —NH(CO)R'; wherein R' represents hydrogen, alkyl or cycloalkyl; and L represents —O—, —S—, —S—CH$_2$—, —SO—, —C≡C—, —NHCO—, —NHCONH— or —NH(SO$_2$)—.

In a more preferred embodiment R represents hydrogen or alkyl; A represents thiadiazolyl, pyridinyl, pyridazinyl, pyrimidinyl or pyrazinyl; and B represents phenyl, furanyl, thienyl or indolyl; which aromatic group may optionally be substituted with hydroxy, alkoxy, halo, trifluoromethyl, cyano or nitro; and L represents —C≡C—.

In a seventh preferred embodiment diazabicycloheptane aryl derivative of the invention is represented by Formula I, wherein R represents hydrogen or alkyl; A represents phenyl, thiadiazolyl, pyridyl or pyridazinyl; B represents a phenyl group, optionally substituted one or two times with substituents selected from the group consisting of alkyl, cycloalkyl, hydroxy, alkoxy, cyanoalkyl, halo, trihaloalkyl, trihaloalkoxy, cyano, amino, nitro, and —NH(CO)R'; wherein R' represents hydrogen, alkyl or cycloalkyl; and L represents —O—, —S—, —S—CH$_2$—, —SO—, —C≡C—, —NHCO—, —NHCONH— or —NH(SO$_2$)—.

In a more preferred embodiment R represents hydrogen or alkyl; A represents pyridazinyl; B represents phenyl, optionally substituted with substituents selected from the group consisting of alkyl, cycloalkyl, hydroxy, alkoxy, cyanoalkyl, halo, trihaloalkyl, trihaloalkoxy, cyano, amino, nitro and —NH(CO)-alkyl; and L represents —O—, —S—, —S—CH$_2$—, —SO—, —C≡C—, —NHCO—, —NHCONH— or —NH(SO$_2$)—.

In an even more preferred embodiment R represents hydrogen or alkyl; A represents pyridazinyl; B represents phenyl, optionally substituted with substituents selected from the group consisting of alkyl, cycloalkyl, hydroxy, alkoxy, cyanoalkyl, halo, trihaloalkyl, trihaloalkoxy, cyano, amino, nitro and —NH(CO)-alkyl; and L represents —C≡C—.

In a most preferred embodiment the diazabicycloheptane aryl derivative of the invention is 2-(6-Phenylethynyl-pyridazin-3-yl)-(1S,4S)-2,5-diaza-bicyclo[2.2.1]heptane;

2-Methyl-5-(6-phenylethynyl-pyridazin-3-yl)-(1S,4S)-2,5-diaza-bicyclo[2.2.1]heptane;

2-[6-(4-Fluoro-phenylethynyl)-pyridazin-3-yl]-5-methyl-(1S,4S)-2,5-diaza-bicyclo[2.2.1]heptane;

2-[6-(4-Methoxy-phenylethynyl)-pyridazin-3-yl]-5-methyl-(1S,4S)-2,5-diaza-bicyclo[2.2.1]heptane;

2-Methyl-5-(5-phenylethynyl-pyrazin-2-yl)-(1S,4S)-2,5-diaza-bicyclo[2.2.1]heptane;

2-Methyl-5-(5-phenylethynyl-pyridin-2-yl)-(1S,4S)-2,5-diaza-bicyclo[2.2.1]heptane;

2-Methyl-5-(5-phenylethynyl-[1,3,4]thiadiazol-2-yl)-(1S,4S)-2,5-diaza-bicyclo[2.2.1]heptane;

2-Methyl-5-(6-thien-2-ylethynyl-pyridazin-3-yl)-(1S,4S)-2,5-diaza-bicyclo[2.2.1]heptane;

2-(6-Furan-2-ylethynyl-pyridazin-3-yl)-5-methyl-(1S,4S)-2,5-diaza-bicyclo[2.2.1]heptane;

2-Methyl-5-(6-thien-3-ylethynyl-pyridazin-3-yl)-(1S,4S)-2,5-diaza-bicyclo[2.2.1]heptane;

2-(6-Furan-3-ylethynyl-pyridazin-3-yl)-5-methyl-(1S,4S)-2,5-diaza-bicyclo[2.2.1]heptane;

2-Methyl-5-(5-phenylethynyl-pyrimidin-2-yl)-(1S,4S)-2,5-diaza-bicyclo[2.2.1]heptane;

2-Methyl-5-(5-phenylethynyl-pyrazin-2-yl)-(1S,4S)-2,5-diaza-bicyclo[2.2.1]heptane; or 5-{6-[5-Methyl-(1S,4S)-2,5-diaza-bicyclo[2.2.1]hept-2-yl]-pyridazin-3-ylethynyl}-1H-indole;

or an enantiomers or a mixture of its enantiomers, or a pharmaceutically acceptable salt thereof.

Any combination of two or more of the embodiments described herein is considered within the scope of the present invention.

Definition of Substituents

In the context of this invention halo represents a fluorine, a chlorine, a bromine or an iodine atom. Thus, a trihalomethyl group represents e.g. a trifluoromethyl group, a trichloromethyl group and similar trihalo-substituted methyl groups.

In the context of this invention an alkyl group designates a univalent saturated, straight or branched hydrocarbon chain. The hydrocarbon chain preferably contain of from one to eighteen carbon atoms ($C_{1-18}$-alkyl), more preferred of from one to six carbon atoms ($C_{1-6}$-alkyl; lower alkyl), including pentyl, isopentyl, neopentyl, tertiary pentyl, hexyl and isohexyl. In a preferred embodiment alkyl represents a $C_{1-4}$-alkyl group, including butyl, isobutyl, secondary butyl, and tertiary butyl. In another preferred embodiment of this invention alkyl represents a $C_{1-3}$-alkyl group, which may in particular be methyl, ethyl, propyl or isopropyl.

In the context of this invention a cycloalkyl group designates a cyclic alkyl group, preferably containing of from three to seven carbon atoms ($C_{3-7}$-cycloalkyl), including cyclopropyl, cyclobutyl, cyclopentyl, cyclohexyl and cycloheptyl.

In the context of this invention a cycloalkyl-alkyl group designates a cycloalkyl group as defined above, which cycloalkyl group is substituted on an alkyl group as also defined above. Examples of preferred cycloalkyl-alkyl groups of the invention include cyclopropylmethyl and cyclopropylethyl.

In the context of this invention an alkoxy group designates an "alkyl-O—" group, wherein alkyl is as defined above. Examples of preferred alkoxy groups of the invention include methoxy and ethoxy.

In the context of this invention a cyanoalkyl group designates an "-alkyl-CN" group, wherein alkyl is as defined above.

In the context of this invention an aromatic monocyclic or bicyclic carbocyclic group designates a monocyclic or polycyclic aromatic hydrocarbon group. Examples of preferred aryl groups of the invention include phenyl, indenyl, naphthyl, azulenyl, fluorenyl, and anthracenyl.

In the context of this invention a 5-6 membered aromatic monocyclic heterocyclic designates a 5-6 membered heteroaryl, which holds one or more heteroatoms in its ring structure. Preferred heteroatoms include nitrogen (N), oxygen (O), and sulphur (S).

Preferred 5-6 membered heteroaryl groups of the invention include furanyl, thienyl, selenophenyl, pyrrolyl (azolyl), oxazolyl, thiazolyl, imidazolyl, pyrazolyl, isoxazolyl, isothiazolyl, oxadiazolyl, triazolyl, thiadiazolyl, pyridyl, pyridazinyl, pyrimidinyl, pyrazinyl, and triazinyl.

More preferred 5 membered heteroaryl groups of the invention include furanyl, thienyl, pyrrolyl (azolyl), oxazolyl, thiazolyl, isoxazolyl, isothiazolyl, and thiadiazolyl.

Most preferred 5 membered heteroaryl groups of the invention include furanyl, thienyl, pyrrolyl, oxazolyl, thiazolyl, imidazolyl, pyrazolyl, isoxazolyl, isothiazolyl, oxadiazolyl, triazolyl and thiadiazolyl.

More preferred 6 membered heteroaryl groups of the invention include pyridyl, pyridazinyl, pyrimidinyl, pyrazinyl and triazinyl.

In the context of this invention an aromatic bicyclic heterocyclic group designates a bicyclic heterocyclic group, which holds one or more heteroatoms in its ring structure. In the context of this invention the term "bicyclic heterocyclic group" includes benzo-fused five- and six-membered heterocyclic rings containing one or more heteroatoms. Preferred heteroatoms include nitrogen (N), oxygen (O), and sulphur (S).

Preferred bicyclic heteroaryl groups of the invention include indolizinyl, indolyl, isoindolyl, benzo[b]furanyl, benzo[b]thienyl, benzoimidazolyl, benzothiazolyl, quinolinyl and isoquinolinyl.

More preferred bicyclic heteroaryl groups of the invention include indolyl, benzo[b]furanyl, benzo[b]thienyl, benzoimidazolyl and benzothiazolyl.

Most preferred bicyclic heteroaryl groups of the invention include indolyl, benzo[b]furanyl, benzo[b]thienyl, and benzothiazolyl.

Pharmaceutically Acceptable Salts

The diazabicycloheptane aryl derivative of the invention may be provided in any form suitable for the intended administration. Suitable forms include pharmaceutically (i.e. physiologically) acceptable salts, and pre- or prodrug forms of the chemical compound of the invention.

Examples of pharmaceutically acceptable addition salts include, without limitation, the non-toxic inorganic and organic acid addition salts such as the hydrochloride, the hydrobromide, the nitrate, the perchlorate, the phosphate, the sulphate, the formate, the acetate, the aconate, the ascorbate, the benzene-sulphonate, the benzoate, the cinnamate, the citrate, the embonate, the enantate, the fumarate, the glutamate, the glycolate, the lactate, the maleate, the malonate, the mandelate, the methanesulphonate, the naphthalene-2-sulphonate derived, the phthalate, the salicylate, the sorbate, the stearate, the succinate, the tartrate, the toluene-p-sulphonate, and the like. Such salts may be formed by procedures well known and described in the art.

Metal salts of a chemical compound of the invention include alkali metal salts, such as the sodium salt of a chemical compound of the invention containing a carboxy group.

In the context of this invention the "onium salts" of N-containing compounds are also contemplated as pharmaceutically acceptable salts. Preferred "onium salts" include the alkyl-onium salts, the cycloalkyl-onium salts, and the cycloalkylalkyl-onium salts.

Steric Isomers

The chemical compounds of the present invention may exist in (+) and (−) forms as well as in racemic forms. The racemates of these isomers and the individual isomers themselves are within the scope of the present invention.

Racemic forms can be resolved into the optical antipodes by known methods and techniques. One way of separating the diastereomeric salts is by use of an optically active acid, and liberating the optically active amine compound by treatment with a base. Another method for resolving racemates into the optical antipodes is based upon chromatography on an optical active matrix. Racemic compounds of the present invention can thus be resolved into their optical antipodes, e.g., by fractional crystallisation of d- or l-(tartrates, mandelates, or camphor-sulphonate) salts for example.

The chemical compounds of the present invention may also be resolved by the formation of diastereomeric amides by reaction of the chemical compounds of the present invention with an optically active activated carboxylic acid such as that derived from (+) or (−) phenylalanine, (+) or (−) phenylglycine, (+) or (−) camphanic acid or by the formation of diastereomeric carbamates by reaction of the chemical compound of the present invention with an optically active chloroformate or the like.

Additional methods for the resolving the optical isomers are known in the art. Such methods include those described by Jaques J, Collet A, & Wilen S in "*Enantiomers, Racemates, and Resolutions*", John Wiley and Sons, New York (1981).

Optical active compounds can also be prepared from optical active starting materials.

Methods of Producing Diazabicyclic Aryl Derivatives

The diazabicycloheptane aryl derivative of the invention may be prepared by conventional methods for chemical synthesis, e.g. those described in the working examples. The starting materials for the processes described in the present application are known or may readily be prepared by conventional methods from commercially available chemicals.

Also one compound of the invention can be converted to another compound of the invention using conventional methods.

The end products of the reactions described herein may be isolated by conventional techniques, e.g. by extraction, crystallisation, distillation, chromatography, etc.

Biological Activity

The present invention is devoted to the provision novel ligands and modulators of the nicotinic receptors, which ligands and modulators are useful for the treatment of diseases or disorders related to the cholinergic receptors, and in particular the nicotinic acetylcholine receptor (nAChR).

Due to their pharmacological profile the compounds of the invention may be useful for the treatment of diseases or conditions as diverse as CNS related diseases, PNS related diseases, diseases related to smooth muscle contraction, endocrine disorders, diseases related to neuro-degeneration, diseases related to inflammation, pain, and withdrawal symptoms caused by the termination of abuse of chemical substances.

In a preferred embodiment the compounds of the invention are used for the treatment of diseases, disorders, or conditions relating to the central nervous system. Such diseases or disorders include cognitive disorders, learning deficit, memory deficits and dysfunction, Alzheimer's disease, attention deficit, attention deficit hyperactivity disorder (ADHD), Tourette's syndrome, psychosis, depression, Bipolar Disorder, mania, manic depression, schizophrenia, cognitive or attention deficits related to schizophrenia, obsessive compulsive disorders (OCD), panic disorders, eating disorders such as anorexia nervosa, bulimia and obesity, narcolepsy, nociception, AIDS-dementia, senile dementia, autism, Parkinson's disease, Huntington's disease, Amyotrophic Lateral Sclerosis, anxiety, non-OCD anxiety disorders, convulsive disorders, epilepsy, neurodegenerative disorders, transient anoxia, induced neuro-degeneration, neuropathy, diabetic neuropathy, periferic dyslexia, tardive dyskinesia, hyperkinesia, mild, pain, moderate or severe pain, pain of acute, chronic or recurrent character, pain caused by migraine, postoperative pain, phantom limb pain, inflammatory pain, neuropathic pain, chronic headache, central pain, pain related to diabetic neuropathy, to post therapeutic neuralgia, or to peripheral nerve injury, bulimia, post-traumatic syndrome, social phobia, sleeping disorders, pseudodementia, Ganser's syndrome, pre-menstrual syndrome, late luteal phase syndrome, chronic fatigue syndrome, mutism, trichotillomania, jet-lag, arrhythmias, smooth muscle contractions, angina pectoris, premature labour, diarrhea, asthma, tardive dyskinesia, hyperkinesia, premature ejaculation, erectile difficulty, hypertension, inflammatory disorders, inflammatory skin disorders, acne, rosacea, Chron's disease, inflammatory bowel disease, ulcerative colitis, diarrhea, or withdrawal symptoms caused by termination of use of addictive substances, including nicotine containing products such as tobacco, opioids such as heroin, cocaine and morphine, benzodiazepines and benzodiazepine-like drugs, and alcohol.

In a more preferred embodiment the disease, disorder or condition is mild, moderate or even severe pain of acute, chronic or recurrent character, pain caused by migraine, postoperative pain, phantom limb pain, inflammatory pain, neuropathic pain, chronic headache, central pain, pain related to diabetic neuropathy, to post therapeutic neuralgia, or to peripheral nerve injury.

In an even more preferred embodiment the disease, disorder or condition are associated with smooth muscle contractions, convulsive disorders, angina pectoris, premature labour, convulsions, diarrhea, asthma, epilepsy, tardive dyskinesia, hyperkinesia, premature ejaculation, or erectile difficulty.

In a still more preferred embodiment the disease, disorder or condition is a neurodegenerative disorder, transient anoxia, or induced neuro-degeneration.

In a yet more preferred embodiment the disease, disorder or condition is an inflammatory disorder, inflammatory skin disorder, acne, rosacea, Chron's disease, inflammatory bowel disease, ulcerative colitis, or diarrhea.

In a further more preferred embodiment the disease, disorder or condition is diabetic neuropathy, schizophrenia, cognitive or attentional deficits related to schizophrenia, or depression.

In a still further more preferred embodiment the disease, disorder or condition is associated withdrawal symptoms caused by termination of use of addictive substances, nicotine containing products, tobacco, opioids, heroin, cocaine, morphine, benzodiazepines or benzodiazepine-like drugs, or alcohol.

In a still further more preferred embodiment the disease, disorder or condition is pain, neuropathic pain, diabetic neuropathy, schizophrenia, cognitive/attentional deficits related to schizophrenia, dementia, or depression.

Finally the compounds of the invention may be useful for the treatment of withdrawal symptoms caused by termination of use of addictive substances. Such addictive substances include nicotine containing products such as tobacco, opioids such as heroin, cocaine and morphine, benzodiazepines and benzodiazepine-like drugs, and alcohol. Withdrawal from addictive substances is in general a traumatic experience characterized by anxiety and frustration, anger, anxiety, difficulties in concentrating, restlessness, decreased heart rate and increased appetite and weight gain.

In this context "treatment" covers treatment, prevention, prophylactics and alleviation of withdrawal symptoms and abstinence as well as treatment resulting in a voluntary diminished intake of the addictive substance.

In another aspect, the compounds of the invention are used as diagnostic agents, e.g. for the identification and localisation of nicotinic receptors in various tissues.

It is at present contemplated that a suitable dosage of the active pharmaceutical ingredient (API) is within the range of from about 0.1 to about 1000 mg API per day, more preferred of from about 10 to about 500 mg API per day, most preferred of from about 30 to about 100 mg API per day, dependent, however, upon the exact mode of administration, the form in which it is administered, the indication considered, the subject and in particular the body weight of the subject involved, and further the preference and experience of the physician or veterinarian in charge.

Preferred compounds of the invention show a biological activity in the sub-micromolar and micromolar range, i.e. of from below 1 to about 100 µM.

Pharmaceutical Compositions

In another aspect the invention provides novel pharmaceutical compositions comprising a therapeutically effective amount of diazabicycloheptane aryl derivative of the invention.

While a chemical compound of the invention for use in therapy may be administered in the form of the raw chemical compound, it is preferred to introduce the active ingredient, optionally in the form of a physiologically acceptable salt, in a pharmaceutical composition together with one or more adjuvants, excipients, carriers, buffers, diluents, and/or other customary pharmaceutical auxiliaries.

In a preferred embodiment, the invention provides pharmaceutical compositions comprising the diazabicycloheptane aryl derivative of the invention, or a pharmaceutically acceptable salt or derivative thereof, together with one or more pharmaceutically acceptable carriers therefore, and, optionally, other therapeutic and/or prophylactic ingredients, know and used in the art. The carrier(s) must be "acceptable" in the sense of being compatible with the other ingredients of the formulation and not harmful to the recipient thereof.

The pharmaceutical composition of the invention may be administered by any convenient route, which suits the desired therapy. Preferred routes of administration include oral administration, in particular in tablet, in capsule, in dragé, in powder, or in liquid form, and parenteral administration, in particular cutaneous, subcutaneous, intramuscular, or intravenous injection. The pharmaceutical composition of the invention can be manufactured by any skilled person by use of standard methods and conventional techniques appropriate to the desired formulation. When desired, compositions adapted to give sustained release of the active ingredient may be employed.

Further details on techniques for formulation and administration may be found in the latest edition of *Remington's Pharmaceutical Sciences* (Maack Publishing Co., Easton, Pa.).

The actual dosage depends on the nature and severity of the disease being treated, and is within the discretion of the physician, and may be varied by titration of the dosage to the particular circumstances of this invention to produce the desired therapeutic effect. However, it is presently contemplated that pharmaceutical compositions containing of from about 0.1 to about 500 mg of active ingredient per individual dose, preferably of from about 1 to about 100 mg, most preferred of from about 1 to about 10 mg, are suitable for therapeutic treatments.

The active ingredient may be administered in one or several doses per day. A satisfactory result can, in certain instances, be obtained at a dosage as low as 0.1 µg/kg i.v. and 1 µg/kg p.o. The upper limit of the dosage range is presently considered to be about 10 mg/kg i.v. and 100 mg/kg p.o. Preferred ranges are from about 0.1 µg/kg to about 10 mg/kg/day i.v., and from about 1 µg/kg to about 100 mg/kg/day p.o.

Methods of Therapy

The diazabicycloheptane aryl derivatives of the present invention are valuable nicotinic and monoamine receptor modulators, and therefore useful for the treatment of a range of ailments involving cholinergic dysfunction as well as a range of disorders responsive to the action of nAChR modulators.

In another aspect the invention provides a method for the treatment, prevention or alleviation of a disease or a disorder or a condition of a living animal body, including a human, which disease, disorder or condition is responsive to modulation of cholinergic receptors and/or monoamine receptors, and which method comprises administering to such a living animal body, including a human, in need thereof an effective amount of an diazabicycloheptane aryl derivative of the invention.

In a preferred embodiment, the disease, disorder or condition relates to the central nervous system.

In a preferred embodiment, the disease, disorder or condition is anxiety, cognitive disorders, learning deficit, memory deficits and dysfunction, Alzheimer's disease, attention deficit, attention deficit hyperactivity disorder, Parkinson's disease, Huntington's disease, Amyotrophic Lateral Sclerosis, Gilles de la Tourette's syndrome, depression, mania, manic depression, schizophrenia, obsessive compulsive disorders (OCD), panic disorders, eating disorders such as anorexia nervosa, bulimia and obesity, narcolepsy, nociception, AIDS-dementia, senile dementia, periferic neuropathy, autism, dyslexia, tardive dyskinesia, hyperkinesia, epilepsy, bulimia, post-traumatic syndrome, social phobia, sleeping disorders, pseudodementia, Ganser's syndrome, pre-menstrual syndrome, late luteal phase syndrome, chronic fatigue syndrome, mutism, trichotillomania, and jet-lag.

In a another preferred embodiment, the disease, disorder or condition are associated with smooth muscle contractions, including convulsive disorders, angina pectoris, premature labour, convulsions, diarrhea, asthma, epilepsy, tardive dyskinesia, hyperkinesia, premature ejaculation, and erectile difficulty.

In a third preferred embodiment, the disease, disorder or condition is related to the endocrine system, such as thyrotoxicosis, pheochromocytoma, hypertension and arrhythmias.

In a fourth preferred embodiment, the disease, disorder or condition is a neurodegenerative disorders, including transient anoxia and induced neuro-degeneration.

In a fifth preferred embodiment, the disease, disorder or condition is an inflammatory disorder, including inflammatory skin disorders such as acne and rosacea, Chron's disease, inflammatory bowel disease, ulcerative colitis, and diarrhea.

In a sixth preferred embodiment, the disease, disorder or condition is mild, moderate or even severe pain of acute, chronic or recurrent character, as well as pain caused by migraine, postoperative pain, and phantom limb pain.

In a seventh preferred embodiment, the disease, disorder or condition is associated with withdrawal symptoms caused by termination of use of addictive substances, including nicotine containing products such as tobacco, opioids such as heroin, cocaine and morphine, benzodiazepines and benzodiazepine-like drugs, and alcohol.

It is at present contemplated that suitable dosage ranges are 0.1 to 1000 milligrams daily, 10-500 milligrams daily, and especially 30-100 milligrams daily, dependent as usual upon the exact mode of administration, form in which administered, the indication toward which the administration is directed, the subject involved and the body weight of the subject involved, and further the preference and experience of the physician or veterinarian in charge.

A satisfactory result can, in certain instances, be obtained at a dosage as low as 0.005 mg/kg i.v. and 0.01 mg/kg p.o. The upper limit of the dosage range is about 10 mg/kg i.v. and 100 mg/kg p.o. Preferred ranges are from about 0.001 to about 1 mg/kg i.v. and from about 0.1 to about 10 mg/kg p.o.

EXAMPLES

The invention is further illustrated with reference to the following examples, which are not intended to be in any way limiting to the scope of the invention as claimed.

Example 1

Preparatory Example

All reactions involving air sensitive reagents or intermediates were performed under nitrogen and in anhydrous solvents. Magnesium sulfate was used as drying agent in the workup-procedures and solvents were evaporated under reduced pressure.

2-[6-Bromo-3-pyridazinyl]-(1S,4S)-5-tert-butoxycarbonyl-2,5-diazabicyclo-[2.2.1]-heptane (Intermediate compound)

A mixture of tert-butyl-(1S,4S)-2,5-diazabicyclo-[2.2.1]-heptane-2-carboxylate (3.0 g; 15.1 mmol), 3,6-dibromopyridazine (3.6 g; 15.1 mmol) and dioxane (15 ml) was stirred for 3 days at 90° C. The crude product salt was filtered. Aqueous sodium hydroxide (50 ml; 1 M) was added to the solid material. The mixture was extracted with dichloromethane (3×50 ml). Chromatography on silica gel with dichloromethane, methanol and conc. ammonia (89:10:1) gave the title compound as free base. Yield 1.71 g (32%).

5-[6-Phenylethynyl-pyridazin-3-yl]-(1S,4S)-2,5-diaza-bicyclo[2.2.1]heptane-2-carboxylic acid tert-butyl ester (Intermediate compound)

A mixture of 2-[6-bromo-3-pyridazinyl]-(1S,4S)-5-tert-butoxycarbonyl-2,5-diazabicyclo-[2.2.1]-heptane (2.0 g; 5.6 mmol), phenylacetylene (2.4 ml; 22.6 mmol), palladacycle (105 mg; 0.11 mmol), CuI (106 mg; 0.56 mmol), diisopropylethylamine (0.97 ml; 5.6 mmol) and dioxane (20 ml) was stirred at 100° C. for 40 hours. Aqueous sodium hydroxide (50 ml; 1 M) was added. The mixture was extracted with dichloromethane (3×50 ml). Chromatography on silica gel with dichloromethane, methanol and conc. ammonia (89:10:1) gave the title compound as free base. Yield 1.0 g (48%).

2-(6-Phenylethynyl-pyridazin-3-yl)-(1S,4S)-2,5-diaza-bicyclo[2.2.1]heptane fumaric acid salt (Compound 1)

A mixture of 5-[6-phenylethynyl-pyridazin-3-yl]-(1S,4S)-2,5-diaza-bicyclo-[2.2.1]heptane-2-carboxylic acid tert-butyl ester (1.95 g; 5.2 mmol), trifluoroacetic acid (8.0 ml; 104 mmol) and dichloromethane (20 ml) was stirred for 2 hours at room temperature. Aqueous sodium hydroxide (20 ml; 4 M) was added. The mixture was extracted with dichloromethane (3×20 ml). Chromatography on silica gel with dichloromethane, methanol and conc. ammonia (89:10:1) gave the title compound as free base. Yield 0.85 g (59%). The corresponding salt was obtained by addition of a diethyl ether and methanol mixture (9:1) saturated with fumaric acid. Mp. 173.1-174.4° C.

2-Methyl-5-(6-phenylethynyl-pyridazin-3-yl)-(1S,4S)-2,5-diaza-bicyclo[2.2.1]heptane fumaric acid salt (Compound 2)

A mixture of 2-(6-phenylethynyl-pyridazin-3-yl)-(1S,4S)-2,5-diaza-bicyclo-[2.2.1]-heptane (0.85 g; 3.1 mmol), formic acid (20 ml) and formaldehyde (20 ml) was stirred at reflux for 15 hours. The mixture was evaporated. Aqueous sodium hydroxide (20 ml; 4 M) was added. The mixture was extracted with dichloromethane (3×20 ml). Chromatography on silica gel with dichloromethane, methanol and conc. ammonia (89:10:1) gave the title compound as free base. Yield 0.25 g (28%). The corresponding salt was obtained by addition of a diethyl ether and methanol mixture (9:1) saturated with fumaric acid. Mp. 211-112° C.

In analogy herewith the following compounds may be synthesized:

2-[6-(4-Fluoro-phenylethynyl)-pyridazin-3-yl]-5-methyl-(1S,4S)-2,5-diaza-bicyclo[2.2.1]heptane;
2-[6-(4-Methoxy-phenylethynyl)-pyridazin-3-yl]-5-methyl-(1S,4S)-2,5-diaza-bicyclo[2.2.1]heptane;
2-Methyl-5-(5-phenylethynyl-pyrazin-2-yl)-(1S,4S)-2,5-diaza-bicyclo[2.2.1]heptane;
2-Methyl-5-(5-phenylethynyl-pyridin-2-yl)-(1S,4S)-2,5-diaza-bicyclo[2.2.1]heptane;
2-Methyl-5-(5-phenylethynyl-[1,3,4]thiadiazol-2-yl)-(1S,4S)-2,5-diaza-bicyclo[2.2.1]heptane;
2-Methyl-5-(6-thien-2-ylethynyl-pyridazin-3-yl)-(1S,4S)-2,5-diaza-bicyclo[2.2.1]heptane;
2-(6-Furan-2-ylethynyl-pyridazin-3-yl)-5-methyl-(1S,4S)-2,5-diaza-bicyclo[2.2.1]heptane;
2-Methyl-5-(6-thien-3-ylethynyl-pyridazin-3-yl)-(1S,4S)-2,5-diaza-bicyclo[2.2.1]heptane;
2-(6-Furan-3-ylethynyl-pyridazin-3-yl)-5-methyl-(1S,4S)-2,5-diaza-bicyclo[2.2.1]heptane;
2-Methyl-5-(5-phenylethynyl-pyrimidin-2-yl)-(1S,4S)-2,5-diaza-bicyclo[2.2.1]heptane;
2-Methyl-5-(5-phenylethynyl-pyrazin-2-yl)-(1S,4S)-2,5-diaza-bicyclo[2.2.1]heptane; and
5-{6-[5-Methyl-(1S,4S)-2,5-diaza-bicyclo[2.2.1]hept-2-yl]-pyridazin-3-ylethynyl}-1H-indole.

Example 2

In vitro Inhibition of $^3$H-α-Bungarotoxine Binding in Rat Brain

In this example the affinity of the compounds of the invention for binding to $α_7$-subtype of nicotinic receptors is determined.

α-Bungarotoxine is a peptide isolated from the venom of the Elapidae snake *Bungarus multicinctus*. It has high affinity for neuronal and neuromuscular nicotinic receptors, where it acts as a potent antagonist. $^3$H-α-Bungarotoxine labels nicotinic acetylcholine receptors formed by the $α_7$ subunit isoform found in brain and the $α_1$ isoform in the neuromuscular junction.

Tissue Preparation

Preparations are performed at 0-4° C. Cerebral cortices from male Wistar rats (150-250 g) are homogenised for 10 seconds in 15 ml of 20 mM Hepes buffer containing 118 mM NaCl, 4.8 mM KCl, 1.2 mM $MgSO_4$ and 2.5 mM $CaCl_2$ (pH 7.5) using an Ultra-Turrax homogeniser. The tissue suspension is subjected to centrifugation at 27,000×g for 10 minutes. The supernatant is discarded and the pellet is washed twice by centrifugation at 27,000×g for 10 minutes in 20 ml of fresh buffer, and the final pellet is then re-suspended in fresh buffer containing 0.01% BSA (35 ml per g of original tissue) and used for binding assays.

Assay

Aliquots of 500 μl of homogenate are added to 25 μl of test solution and 25 μl of $^3$H-α-bungarotoxine (2 nM, final con-centration) and mixed and incubated for 2 hours at 37° C. Non-specific binding is determined using (−)-nicotine (1 mM, final con-centration). After incubation, the samples are added 5 ml of ice-cold Hepes buffer containing 0.05% PEI and poured directly onto Whatman GF/C glass fibre filters (pre-soaked in 0.1% PEI for at least 6 hours) under suction, and immediately washed with 2×5 ml ice-cold buffer.

The amount of radioactivity on the filters is determined by conventional liquid scintillation counting. Specific binding is total binding minus non-specific binding.

The test value is given as an $IC_{50}$ (the concentration of the test substance which inhibits the specific binding of $^3$H-α-bungarotoxin by 50%).

The results of these experiments are presented in Table 1 below.

TABLE 1

Inhibition of $^3$H-α-Bungarotoxine Binding

| Compound No. | IC$_{50}$ (μM) |
|---|---|
| 2 | 2.0 |

The invention claimed is:

1. A (R,R) or (S,S) 2,5-diaza-bicyclo[2.2.1]heptane aryl compound represented by Formula I

R—N⟨⟩N—A—L—B  (I)

or an enantiomer or a mixture of its enantiomers, or a pharmaceutically acceptable salt thereof, wherein R represents hydrogen, alkyl, cycloalkyl or cycloalkylalkyl;

A represents an aromatic monocyclic or bicyclic carbocyclic or heterocyclic group, which carbocyclic or heterocyclic groups are optionally substituted one or more times with substituents selected from the group consisting of alkyl, cycloalkyl, cycloalkyl-alkyl, hydroxy, alkoxy, cyanoalkyl, halo, trihaloalkyl, trihaloalkoxy, cyano, amino and nitro;

B represents a phenyl or naphthyl group, a 5-6 membered aromatic monocyclic heterocyclic group, or an aromatic bicyclic heterocyclic group; which aromatic groups may optionally be substituted one or more times with substituents selected from the group consisting of alkyl, cycloalkyl, hydroxy, alkoxy, cyanoalkyl, halo, trihaloalkyl, trihaloalkoxy, cyano, amino, nitro, and —NH(CO)R'; wherein R' represents hydrogen, alkyl or cycloalkyl; and L represents —O—, —S—, —S—CH$_2$—, —CH$_2$—S—, —SO—, —SO$_2$—, —NR"—, —CH$_2$—, —CH$_2$—CH$_2$—, —CH═CH—, —C≡C—, —NR"CO—, —NR"CONR"— or —NR"(SO$_2$)—; wherein R" represents hydrogen or alkyl.

2. The diazabicycloheptane aryl compound of claim 1, or an enantiomer or a mixture of its enantiomers or a pharmaceutically acceptable salt thereof, wherein R represents hydrogen, alkyl, cycloalkyl or cycloalkyl-alkyl.

3. The diazabicycloheptane aryl compound of claim 1, or an enantiomer or a mixture of its enantiomers or a pharmaceutically acceptable salt thereof, wherein A represents an aromatic monocyclic or bicyclic carbocyclic or heterocyclic group, which carbocyclic or heterocyclic groups are optionally substituted one or more times with substituents selected from the group consisting of alkyl, cycloalkyl, cycloalkyl-alkyl, hydroxy, alkoxy, cyanoalkyl, halo, trihaloalkyl, trihaloalkoxy, cyano, amino and nitro.

4. The diazabicycloheptane aryl compound of claim 3, or an enantiomer or a mixture of its enantiomers or a pharmaceutically acceptable salt thereof, wherein A represents a phenyl group.

5. The diazabicycloheptane aryl compound of claim 3, or an enantiomer or a mixture of its enantiomers or a pharmaceutically acceptable salt thereof, wherein A represents a 5-membered aromatic monocyclic heterocyclic group selected from furanyl, thienyl, pyrrolyl, oxazolyl, thiazolyl, imidazolyl, pyrazolyl, isoxazolyl, isothiazolyl, oxadiazolyl, triazolyl and thiadiazolyl.

6. The diazabicycloheptane aryl compound of claim 3, or an enantiomer or a mixture of its enantiomers or a pharmaceutically acceptable salt thereof, wherein A represents a 6-membered aromatic monocyclic heterocyclic group selected from pyridinyl, pyridazinyl, pyrimidinyl, pyrazinyl and triazinyl.

7. The diazabicycloheptane aryl compound of claim 3, or an enantiomer or a mixture of its enantiomers or a pharmaceutically acceptable salt thereof, wherein A represents a thiadiazolyl, a pyridinyl, a pyridazinyl, a pyrimidinyl or a pyrazinyl group.

8. The diazabicycloheptane aryl compound of claim 1, or an enantiomer or a mixture of its enantiomers or a pharmaceutically acceptable salt thereof, wherein B represents a phenyl or naphthyl group, a 5-6 membered aromatic monocyclic heterocyclic group, or an aromatic bicyclic heterocyclic group; which aromatic groups may optionally be substituted one or more times with substituents selected from the group consisting of alkyl, cycloalkyl, hydroxy, alkoxy, cyanoalkyl, halo, trihaloalkyl, trihaloalkoxy, cyano, amino, nitro, and —NH(CO)R'; wherein R' represents hydrogen, alkyl or cycloalkyl.

9. The diazabicycloheptane aryl compound of claim 8, or an enantiomer or a mixture of its enantiomers or a pharmaceutically acceptable salt thereof, wherein B represents a phenyl group, a furanyl group, a thienyl group or an indolyl group; which aromatic group may optionally be substituted one or two times with substituents selected from the group consisting of alkyl, cycloalkyl, hydroxy, alkoxy, cyanoalkyl, halo, trihaloalkyl, trihaloalkoxy, cyano, amino, nitro, and —NH(CO)R'; wherein R' represents hydrogen, alkyl or cycloalkyl.

10. The diazabicycloheptane aryl compound of claim 1, or an enantiomer or a mixture of its enantiomers or a pharmaceutically acceptable salt thereof wherein R represents hydrogen or alkyl;

A represents thiadiazolyl, pyridinyl, pyridazinyl, pyrimidinyl or pyrazinyl; and B represents phenyl, furanyl, thienyl or indolyl; which aromatic group may optionally be substituted one or two times with substituents selected from the group consisting of alkyl, cycloalkyl, hydroxy, alkoxy, cyanoalkyl, halo, trihaloalkyl, trihaloalkoxy, cyano, amino, nitro, and —NH(CO)R'; wherein R' represents hydrogen, alkyl or cycloalkyl.

11. The diazabicycloheptane aryl compound of claim 1, or an enantiomer or a mixture of its enantiomers or a pharmaceutically acceptable salt thereof, wherein L represents —O—, —S—, —S—CH$_2$—, —CH$_2$—S—, —SO—, —SO$_2$—, —NR"—, CH$_2$—, —CH$_2$—CH$_2$—, —CHCH—, —C≡C—, —NR"CO—, —NR"CONR"— or —NR"(SO$_2$)—; wherein R" represents hydrogen or alkyl.

12. The diazabicycloheptane aryl compound of claim 11, or an enantiomer or a mixture of its enantiomers or a pharmaceutically acceptable salt thereof, wherein L represents —O—, —S—, —S—CH$_2$—, —SO—, —C≡C—, —NHCO—, —NHCONH— or —NH(SO$_2$)—.

13. The diazabicycloheptane aryl compound of claim 1, or an enantiomer or a mixture of its enantiomers or a pharmaceutically acceptable salt thereof, wherein R represents hydrogen or alkyl;

A represents thiadiazolyl, pyridinyl, pyridazinyl, pyrimidinyl or pyrazinyl; and B represents phenyl, furanyl, thienyl or indolyl; which aromatic group may optionally be substituted one or two times with substituents selected from the group consisting of alkyl, cycloalkyl, hydroxy, alkoxy, cyanoalkyl, halo, trihaloalkyl, trihaloalkoxy, cyano, amino, nitro, and —NH(CO)R'; wherein R' represents hydrogen, alkyl or cycloalkyl; and L represents —O—, —S—, —S—CH$_2$—, —SO—, —C≡C—, —NHCO—, —NHCONH— or —NH(SO$_2$)—.

14. A (R,R) or (S,S) 2,5-diaza-bicyclo[2.2.1]heptane aryl compound represented by Formula I

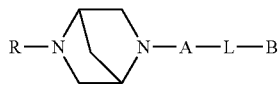

(I)

or an enantiomer or a mixture of its enantiomers, or a pharmaceutically acceptable salt thereof, wherein R represents hydrogen or alkyl;

A represents thiadiazolyl, pyridinyl, pyridazinyl, pyrimidinyl or pyrazinyl;

B represents phenyl, furanyl, thienyl or indolyl; which aromatic group may optionally be substituted one or two times with substituents selected from the group consisting of alkyl, cycloalkyl, hydroxy, alkoxy, cyanoalkyl, halo, trihaloalkyl, trihaloalkoxy, cyano, amino, nitro, and —NH(CO)R'; wherein R' represents hydrogen, alkyl or cycloalkyl; and L represents —O—, —S—, —S—CH$_2$—, —SO—, —C≡C—, —NHCO—, —NHCONH— or —NH(SO$_2$)—, said compound being:

2-(6-Phenylethynyl-pyridazin-3-yl)-(1S,4S)-2,5-diaza-bicyclo[2.2.1]heptane;
2-Methyl-5-(6-phenylethynyl-pyridazin-3-yl)-(1S,4S)-2,5-diaza-bicyclo[2.2.1]heptane;
2-[6-(4-Fluoro-phenylethynyl)-pyridazin-3-yl]-5-methyl-(1S,4S)-2,5-diaza-bicyclo[2.2.1]heptane;
2-[6-(4-Methoxy-phenylethynyl)-pyridazin-3-yl]-5-methyl-(1S,4S)-2,5-diaza-bicyclo[2.2.1]heptane;
2-Methyl-5-(5-phenylethynyl-pyrazin-2-yl)-(1S,4S)-2,5-diaza-bicyclo[2.2.1]heptane;
2-Methyl-5-(5-phenylethynyl-pyridin-2-yl)-(1S,4S)-2,5-diaza-bicyclo[2.2.1]heptane;
2-Methyl-5-(5-phenylethynyl-[1,3,4]thiadiazol-2-yl)-(1S,4S)-2,5-diaza-bicyclo[2.2.1]heptane;
2-Methyl-5-(6-thien-2-ylethynyl-pyridazin-3-yl)-(1S,4S)-2,5-diaza-bicyclo[2.2.1]heptane;
2-(6-Furan-2-ylethynyl-pyridazin-3-yl)-5-methyl-(1S,4S)-2,5-diaza-bicyclo[2.2.1]heptane;
2-Methyl-5-(6-thien-3-ylethynyl-pyridazin-3-yl)-(1S,4S)-2,5-diaza-bicyclo[2.2.1]heptane;
2-(6-Furan-3-ylethynyl-pyridazin-3-yl)-5-methyl-(1S,4S)-2,5-diaza-bicyclo[2.2.1]heptane;
2-Methyl-5-(5-phenylethynyl-pyrimidin-2-yl)-(1S,4S)-2,5-diaza-bicyclo[2.2.1]heptane;
2-Methyl-5-(5-phenylethynyl-pyrazin-2-yl)-(1S,4S)-2,5-diaza-bicyclo[2.2.1]heptane; or
5-{6-[5-Methyl-(1S,4S)-2,5-diaza-bicyclo[2.2.1]hept-2-yl]-pyridazin-3-ylethynyl}-1H-indole;

or an enantiomers or a mixture of its enantiomers, or a pharmaceutically acceptable salt thereof.

15. A pharmaceutical composition comprising a therapeutically effective amount of a diazabicycloheptane aryl compound of claim 1, or an enantiomer or a mixture of its enantiomers or a pharmaceutically-acceptable addition salt thereof, together with at least one pharmaceutically-acceptable carrier or diluent.

16. A (R,R) or (S,S) 2,5-diaza-bicyclo[2.2.1]heptane aryl compound represented by Formula I

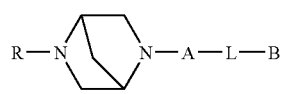

(I)

or an enantiomer or a mixture of its enantiomers, or a pharmaceutically acceptable salt thereof, wherein R represents hydrogen or alkyl;

A represents thiadiazolyl, pyridinyl, pyridazinyl, pyrimidinyl or pyrazinyl;

B represents phenyl, furanyl, thienyl or indolyl; which aromatic group may optionally be substituted one or two times with substituents selected from the group consisting of alkyl, cycloalkyl, hydroxy, alkoxy, cyanoalkyl, halo, trihaloalkyl, trihaloalkoxy, cyano, amino, nitro, and —NH(CO)R'; wherein R' represents hydrogen, alkyl or cycloalkyl; and L represents —O—, —S—, —S—CH$_2$—, —SO—, —C≡C—, —NHCO—, —NHCONH— or —NH(SO$_2$)—, said compound being 2-(6-Phenylethynyl-pyridazin-3-yl)-(1S,4S)-2,5-diaza-bicyclo[2.2.1]heptane, or an enantiomer or a mixture of its enantiomers, or a pharmaceutically acceptable salt thereof.

* * * * *